United States Patent [19]

Mitra

[11] 4,163,777
[45] Aug. 7, 1979

[54] CONTROLLED ANTACID DELIVERY FORM AND METHOD OF TREATMENT THEREWITH

[75] Inventor: Arun K. Mitra, St. Louis, Mo.

[73] Assignee: Lewis/Howe Company, St. Louis, Mo.

[21] Appl. No.: 792,101

[22] Filed: Apr. 29, 1977

[51] Int. Cl.² .......................... A61K 9/24; A61K 9/22
[52] U.S. Cl. ........................................ 424/21; 424/19; 424/127; 424/128; 424/155; 424/156; 424/157; 424/317; 424/319
[58] Field of Search ........................... 424/19, 157, 21

[56] References Cited

U.S. PATENT DOCUMENTS

| | | |
|---|---|---|
| 3,555,151 | 1/1971 | Kaplan et al. ..................... 424/151 |
| 3,590,117 | 6/1971 | Christenson et al. ................ 424/19 |
| 3,626,393 | 12/1971 | Nakamoto et al. ................... 424/19 |
| 3,641,236 | 2/1972 | Coppen et al. ...................... 424/19 |
| 3,773,920 | 11/1973 | Nakamoto et al. ................... 424/19 |
| 3,870,790 | 3/1975 | Lowey et al. ....................... 424/19 |

FOREIGN PATENT DOCUMENTS

| | | | |
|---|---|---|---|
| 1524034 | 4/1968 | France ..................................... 424/19 |
| 837451 | 6/1960 | United Kingdom ..................... 424/19 |
| 862376 | 3/1961 | United Kingdom ..................... 424/19 |
| 1171691 | 11/1969 | United Kingdom ..................... 424/19 |

*Primary Examiner*—Frederick E. Waddell

[57] ABSTRACT

A controlled antacid delivery form having an acid neutralizing component in a matrix including a gel-forming, swelling agent and a water insoluble lipid material. These materials are mixed with the antacid component, together with a large amount of sweet excipient, and compressed at high pressure to provide an antacid lozenge which dissolves very slowly in the mouth.

A method for controlled antacid delivery wherein the controlled antacid delivery form is slowly dissolved in the mouth and neutralizes the stomach acid over a long period of time with surprising little antacid, while bathing the esophageal lining with antacid. When the controlled antacid delivery form includes a mixture of antacids having different reactivities towards acid, said method provides for substantially complete utilization of each component.

4 Claims, 1 Drawing Figure

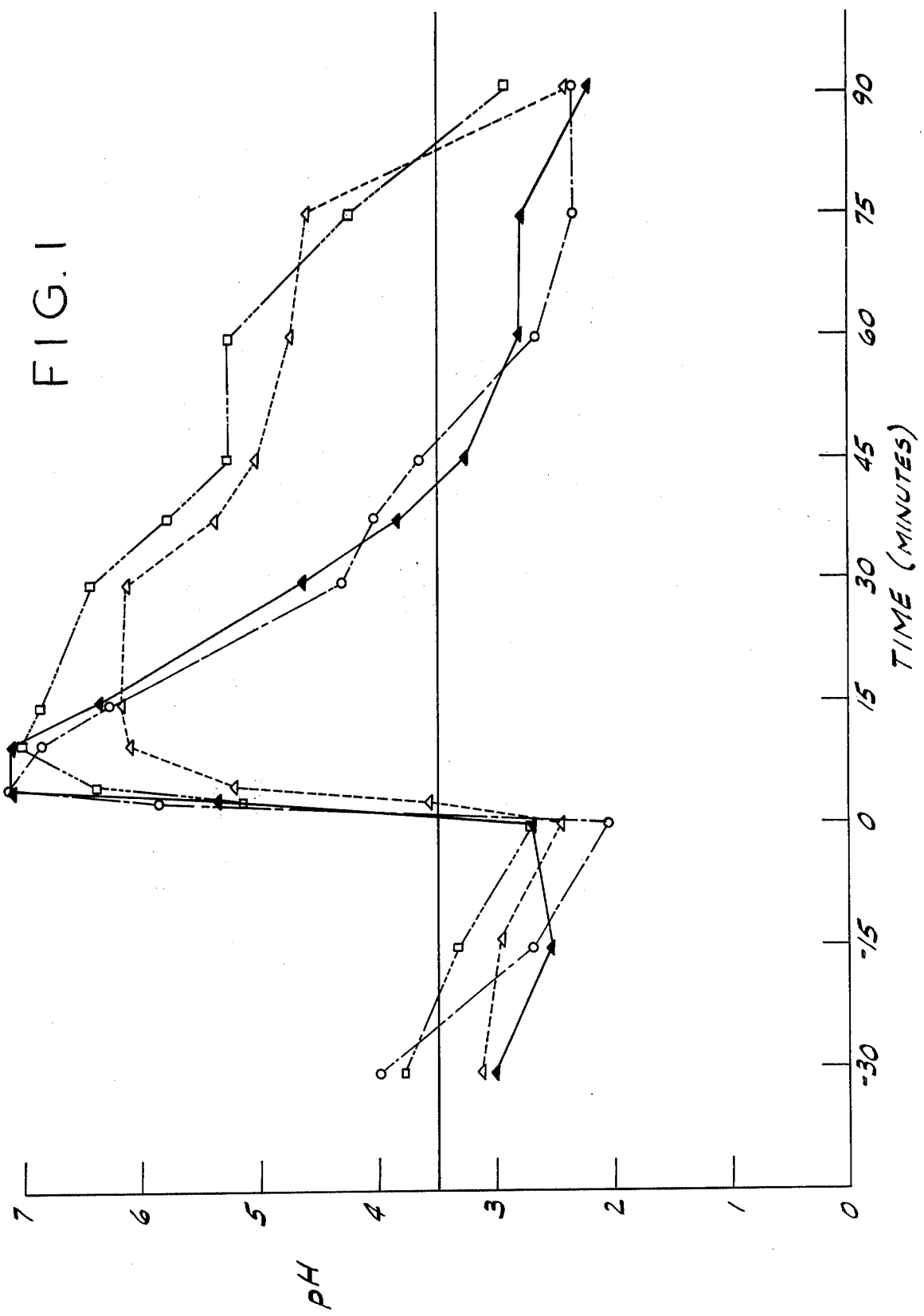

CONTROLLED ANTACID DELIVERY FORM AND METHOD OF TREATMENT THEREWITH

This invention relates to a controlled antacid delivery form and to a method for the controlled administration of antacid. More particularly, a slowly dissolving antacid dosage form is obtained from an acid neutralization component in a matrix including a sugar or a sugar alcohol, a gel-forming, swelling agent and a water insoluble lipid material. When these materials are mixed with the antacid component, together with conventional tableting binders, lubricants and other excipients, and compressed at high pressure, they yield an antacid lozenge which dissolves very slowly in the mouth. When the sweet excipient is a sugar alcohol, the lozenge is "sugarless" and desirably noncariogenic.

As the controlled dosage form is slowly dissolved in the mouth, a sustained release of antacid is obtained which unexpectedly neutralized the stomach acid over a long period of time with surprisingly little antacid. When the lozenge includes a mixture of antacids with different reactivities such as the magnesium and aluminum salts, this invention also involves the discovery that such dosage form provides for more complete utilization of the antacid than is possible with conventional antacids. Administration of the present dosage form also provides for more effective treatment since the gradual release of antacid off-sets the effect of stomach emptying and continuous secretion of acid. It also continuously bathes the lining of the esophagus and provides relief for tissues inflamed by gastric reflux.

With conventional antacids, whether in liquid, powder or tablet form, the entire dose is ingested at one time. They, therefore, have only brief therapeutic effect because the stomach is constantly emptying and secreting more hydrochloric acid. The amount of antacid actually utilized can be as small as 10 to 15 percent and is generally no greater than 50 to 60 percent. The exact amount depends upon the amount of the antacid, its dosage form, the individual patient and the time he ingests the medication.

Many commercially available antacids contain a mixture of magnesium and aluminum salts. It has now been discovered and is disclosed herein that when there is an excess of antacid, the acid preferentially reacts with the magnesium component and the beneficial effect expected from the admixture is thus subverted. More particularly, when 20 to 40 percent of the antacid is consumed, only the magnesium component reacts with the acid while the aluminum shows almost no reactivity. Since no more than 50 to 60 percent of a conventional antacid is actually utilized in the stomach, there is substantially no benefit gained from the combination of such metal salts where the entire dose is ingested at one time. This is wasteful of the aluminum salts and may cause undesirable side effects through phosphate binding in the intestines.

The standard recommended dose for most commercially available antacids is "1 to 2 teaspoonfuls" or "1 to 2 tablets" three times daily, after meals and at bedtime. Such recommendation is given scant attention by laymen and physicians. For example, some gastroenterologists prescribe 3 to 6 teaspoonfuls every waking hour for peptic ulcer patients.

It has also been discovered and is disclosed herein that there is substantially no benefit gained from such overdosing. On the contrary, massive overdoses can produce undesirable side effects. For example, excessive amounts of magnesium can cause hypermagnesia and diarrhea. As mentioned above, excessive amounts of aluminum can cause phosphate binding, which is extreme cases can result in electrolytic imbalance, bone embrittlement, lethargy and labored gait. Too much calcium can cause hypercalcemia, milk-alkali syndrome and Burnett's syndrome. The effect of borderline overdosage, particularly if chronic, is less well documented but is suspected to be a serious medical problem.

In view of the above, it is an object of the present invention to provide a controlled antacid dosage form, as well as to provide for the controlled administration of a mixture of antacids such that all components neutralize the acid and the benefits of the combination are thus obtained. In its preferred form, a slowly dissolving lozenge is provided of a size and shape so that it can be comfortably retained in the mouth for extended periods of time. It is a further object to provide a controlled dosage form which when administered in accordance with the present invention provides better antacid therapy with surprisingly little antacid than obtained even with a massive overdose of a conventional antacid and which off-sets the effect of stomach emptying and continuous secretion of acid. It is a still further object to provide a dosage form which provides relief to patients suffering from esophageal inflammation caused by gastric reflux. Other objects and features will be in part apparent and in part pointed out hereinafter.

The invention accordingly comprises the products and methods hereinafter described, the scope of the invention being indicated in the subjoined claims.

In dosage forms according to the present invention, the antacid component, or acid neutralizing substance, can be any of various nontoxic sodium, calcium, magnesium or aluminum salts used to neutralize gastric fluids. Illustrative antacids are sodium bicarbonate, sodium citrate, calcium carbonate, calcium phosphate, magnesium oxide, magnesium hydroxide, magnesium carbonate, magnesium trisilicate, aluminum carbonate and aluminum hydroxide. Other suitable antacids include dihydroxy aluminum sodium carbonate, dihydroxy aluminum aminoacetate and magnesium hydroxy aluminates. Various other coprecipitates of aluminum hydroxides or carbonates with magnesium hydroxides or carbonates, hexitols, aminoacetic acid or the like can be used. As in the most frequently prescribed antacids, it is preferred that the neutralizing substance in the present dosage form be a combination of magnesium and aluminum salts. This combination is preferred because it provides an antacid with the characteristics of both metals.

The gel-forming, swelling agents used with the above-mentioned antacids are those pharmaceutically acceptable high molecular weight substances which swell and form a gel upon contact with water. Such gel-forming, swelling agents include various gums, polysaccharides, cellulose derivatives and the like. Specific examples of gums are gum acacia, gum tragacanth, guar gum and xanthan gum. Exemplary polysaccharides include the carageenans and alginic acid and its derivatives such as sodium alginate and propylene glycol alginate. Suitable cellulose derivatives include methyl cellulose, hydroxyethyl cellulose, hydroxypropyl cellulose, hydroxypropylmethyl cellulose and sodium carboxymethyl cellulose. Of those materials listed above, sodium carboxymethyl cellulose is particularly preferred for use herein.

The water insoluble lipid material for use in combination with the gel-forming, swelling agents is a hydrophobic metal salt of a fatty acid such as stearic acid, palmetic acid, oleic acid and lauric acid. Applicable metals for formation of the above salts include magnesium, calcium and aluminum. Of these materials, magnesium and calcium stearate are preferred.

Dosage forms according to this invention are preferably formulated from a granulation containing the antacid and a sweet tasting excipient. To this granulation, which may contain additional materials such as gelatin or starch, is added the gel-forming, swelling agent and the water insoluble lipid material. If desired, part of the gel-forming, swelling agent may be dissolved and incorporated in the granulation. Other materials such as talc, flavorants, dyes or the like may be added to the granulation before the mixture is compressed into lozenges.

Since the product is intended to be slowly dissolved in the mouth, it is important that the lozenge contain a large amount of a good tasting excipient. Suitable good tasting, sweet excipients include the sugar alcohols mannitol, sorbitol and xylitol. Sugar alcohols are particularly preferred for use herein because they provide lozenges which are "sugarless" and, hence, noncariogenic. Of the sugar alcohols mentioned above, mannitol is best suited because it is less soluble than sorbitol. It provides a slightly sweet product with a particularly refreshing taste because of its negative heat of solution. Moreover, products formed therewith have better shelf life because mannitol, unlike sorbitol, is not hygroscopic.

When the sweet excipient is an alcohol sugar, it may be necessary to add an artificial sweetener to provide a lozenge with an acceptable taste. While mannitol is preferred, it may be substituted by or used in combination with other sugar alcohols. If a candy like lozenge is wanted, sucrose, dextrose or the like may be used in place of the sugar alcohol. Since these sugars are more soluble than mannitol, the amount of the gel-forming, swelling agent and the amount of the water insoluble lipid material must be increased to provide lozenges with comparable dissolving times.

The antacid is provided in a sufficient quantity to effect neutralization of the acid over the selected period. For use in accordance with this invention, that period is from 15 to 60 minutes, preferably from 30 to 60 minutes. To that end each lozenge has from 15 to 40 meq. of antacid, preferably from 20 to 30 meq.

The amount of sweet excipient is selected to give the lozenge a pleasantly sweet taste. For the purpose, the sweet excipient makes up 25 to 60 percent by weight of the lozenge, preferably from 35 to 50. When the excipient is mannitol, it is most preferably present in an amount from about 30 to 55 percent.

The amount of the gel-forming, swelling agent and the amount of the water insoluble lipid material varies with the particular agents selected. They should be present, however, in combination in a sufficient amount so that the lozenge will slowly dissolve and administer the antacid in the requisite time. Since the patient usually works the lozenge with his tongue and teeth, there is a continuous erosion of the lozenge so that the dissolution time in vivo is usually much shorter than in vitro even with good agitation.

The gel-forming, swelling agent when hydrated forms a film barrier through which the antacid is slowly diffused. If no water insoluble lipid material is added, a satisfactory lozenge cannot be formed. That is, when sufficient gel-forming, swelling agent is added to control the release time, the lozenge has a slimy, unpalatable mouth feel. On the other hand, if no gel-forming, swelling agent is added, the gritty feel and astringent taste of the antacid is exposed. By providing a proper balance of said agents, it is possible to provide a controlled antacid delivery form which is palatable.

When the gel-forming, swelling agent is medium viscosity grade sodium carboxymethyl cellulose, it is preferably present in an amount from about 3 to 10 percent by weight. If larger amounts are used, for example 15 to 20 percent, the lozenge has an unacceptable gummy texture. Amounts less than 3 percent do not sufficiently slow dissolution and amounts over 10 percent produce a slimy feeling.

When the water insoluble lipid material is calcium or magnesium stearate, it is preferably present in an amount from about 1 to 5 percent by weight. Amounts less than 1 percent do not sufficiently slow dissolution and amounts over 5 percent are likely to interfere with the antacid activity in the stomach.

The compressive force with which the lozenges are formed, as well as the surface area and hence the shape, also has an important effect on dissolution times. Mass of the tablet is also important. Lozenges in accordance with the present invention have a hardness of at least 15 kg/in.$^2$ as determined with a modified Herberlein hardness tester. As modified, one of the testing jaws has a V-shaped indentation for registry with a correspondingly V-shaped protrusion on the other jaw. Such lozenges can be formed on a Stokes tableting machine at approximately 7 tons pressure into pieces weighing between 1 and 3 g. with $\frac{5}{8}$ in. punches having deep concave faces. Similar tablets can be made with a Carver laboratory press at a pressure of 3,600 psi. Although the above-described methods of manufacture are efficacious, they are merely illustrative.

The controlled antacid delivery form of this invention can also contain other excipients or therapeutic substances.

The preparations of this invention are particularly useful in antacid therapy since the gradual release of antacid off-sets the effect of stomach emptying and constant secretion of acid. When the lozenge contains a mixture of antacids having different reactivities, the present invention provides for substantially complete utilization of all of the antacid components. It is also useful in the treatment of reflux esophagitis and heartburn.

The following examples illustrate the invention:

EXAMPLE 1

A wet granulation having the composition shown in Table 1 was prepared as follows: The mannitol, aluminum hydroxide-magnesium carbonate coprecipitate and magnesium carbonate were mixed in a twin shell blender for 5 minutes. The gelatin was dissolved in water and heated to 60° C. The gelatin solution was mixed with the above-described blend in a Simpson mixmuller to form a wet granulation. The wet granulation was spread on a tray and dried at 60° C. for 8 hours. The dried granulation was then passed through a Erweka granulator to reduce the dried material to an 18 mesh or finer particle size. This dried material is called the raw granulation.

Table 1

| Raw Granulation | |
| --- | --- |
| Ingredient | Percent |
| Mannitol Powder | 48.17 |
| Aluminum Hydroxide-Magnesium Carbonate Coprecipitate | 25.74 |
| Magnesium Carbonate | 21.76 |
| Gelatin Solution, 10% weight/weight | 4.33 |
| | 100.00 |

Lozenges having the composition shown in Table 2 were prepared as follows: The raw granulation, sodium carboxymethyl cellulose, calcium stearate, talc and flavorant were mixed for 15 minutes in a twin shell blender. This mixture was then made into lozenges on a Stokes RD-3 tablet press with ⅝ in. die and deep concave punches at a pressure of 7 tons.

Table 2

| Lozenge Formula | |
| --- | --- |
| Ingredient | Percent |
| Raw Granulation | 91.33 |
| Sodium Carboxymethyl Cellulose[1] | 5.00 |
| Calcium Stearate | 1.00 |
| Talc | 1.00 |
| Flavorant | 1.67 |
| | 100.00 |

[1] medium viscosity grade

The lozenges formed in accordance with this example were very hard, beyond the normal scale range for a Pfizer, Erweka or Heberlein tablet hardness tester. The average time to dissolve the lozenge in the mouth was approximately 50 minutes. They had a sweet, pleasant taste with no unpalatable slimy or gritty mouth feel. These lozenges had 18 meq. of antacid neutralizing capacity.

EXAMPLE 2

A raw granulation having the composition shown in Table 3 was prepared according to the procedure of Example 1 except that calcium carbonate was used as the antacid component and starch paste was used as the auxiliary binder. The wet granulation was dried at 60° C. for 24 hours.

Table 3

| Raw Granulation | |
| --- | --- |
| Ingredient | Percent |
| Mannitol Powder | 19.63 |
| Calcium Carbonate | 76.45 |
| Starch Pate, 10% weight/weight | 3.92 |
| | 100.0 |

Lozenges having a slow dissolving layer and a fast dissolving layer with the composition shown in Tables 4 and 5, respectively, were prepared as in example 1 except that the slow and fast mixtures were loaded into a Manesty double-layer tablet press with ⅝ in. die and deep concave punches. The machine was adjusted so that the slow dissolving layer weighed 1.8 g. and the fast dissolving layer weighed 0.8 g.

Table 4

| Slowing Dissolving Layer | |
| --- | --- |
| Ingredient | Percent |
| Raw Granulation | 54.5 |
| Sodium Carboxymethyl Cellulose | 4.0 |
| Calcium Stearate | 1.1 |

Table 4-continued

| Slowing Dissolving Layer | |
| --- | --- |
| Ingredient | Percent |
| Granular Sorbitol | 39.6 |
| Flavorant | 0.8 |
| | 100.00 |

Table 5

| Fast Dissolving Layer | |
| --- | --- |
| Ingredient | Percent |
| Raw Granulation | 42.00 |
| Sorbitol granular | 52.66 |
| Calcium Stearate | 0.10 |
| Talc | 0.40 |
| Colorant | 0.30 |
| Primogel | 4.00 |
| Flavorant | 0.54 |
| | 100.00 |

The lozenges formed in accordance with this example were very hard. The slow dissolving layer is in accordance with the invention, the fast dissolving layer is not. The fast dissolving layer dissolved in less than 5 minutes. The dissolution time for the entire double-layer lozenge in the mouth was approximately 20 minutes. The lozenge had a pleasant taste with no unpalatable slimy or gritty mouth feel.

EXAMPLE 3 a raw granulation having the composition shown in Table 6 was prepared according to the procedure of Example 1 except that calcium carbonate was included as part of the antacid component and starch paste was used as the auxiliary binder.

Table 6

| Raw Granulation | |
| --- | --- |
| Ingredient | Percent |
| Mannitol Powder | 53.87 |
| Aluminum Hydroxide-Magnesium Carbonate Coprecipitate | 9.43 |
| Magnesium Carbonate | 13.47 |
| Calcium Carbonate | 18.52 |
| Starch Paste, 10% weight/weight | 4.71 |
| | 100.00 |

Lozenges having the composition shown in Table 7 were prepared following the procedure of Example 1.

Table 7

| Lozenge Formula | |
| --- | --- |
| Ingredient | Percent |
| Raw Granulation | 93.34 |
| Sodium Carboxymethyl Cellulose | 3.00 |
| Calcium Stearate | 1.00 |
| Talc | 1.00 |
| Flavorant | 1.66 |
| | 100.00 |

The lozenges were hard, slow dissolving and had 24 meq. of antacid neutralizing capacity. They had a sweet, pleasant taste with no unpalatable slimy or gritty mouth feel. They weighed 2 g. and had a dissolution time of 47 minutes.

EXAMPLE 4

A raw granulation having the composition shown in Table 8 was prepared according to the procedure of Example 1 except that magnesium hydroxide was substituted for the magnesium carbonate and sorbitol was substituted for part of the mannitol.

Table 8

| Raw Granulation | |
|---|---|
| Ingredient | Percent |
| Mannitol Powder | 31.53 |
| Sorbitol Solution, 10% weight/weight[(1)] | 4.74 |
| Aluminum Hydroxide-Magnesium Carbonate Coprecipitate | 14.24 |
| Magnesium Hydroxide | 42.37 |
| Gelatin Solution, 15% weight/weight[(1)] | 7.12 |
| | 100.00 |

[(1)]Added as a sorbitol and gelatin solution which was 10% weight/weight in sorbitol and 15% weight/weight in gelatin.

Lozenges having the composition shown in Table 9 were prepared following the procedure of Example 1.

Table 9

| Lozenge Formula | |
|---|---|
| Ingredient | Percent |
| Raw Granulation | 90.34 |
| Sodium Carboxymethyl Cellulos | 5.00 |
| Calcium Stearate | 2.00 |
| Talc | 1.00 |
| Flavorant | 1.66 |
| | 100.00 |

The lozenges had 33 meq. of acid neutralizing capacity and took an average time of 50 minutes to dissolve in the mouth.

EXAMPLE 5

A raw granulation having the composition shown in Table 10 was prepared according to the procedure of Example 1 except that powdered sugar was substituted for the mannitol powder.

Table 10

| Raw Granulation | |
|---|---|
| Ingredient | Percent |
| Powdered Sugar | 49.17 |
| Aluminum Hydroxide-Magnesium Carbonate Coprecipitate | 26.26 |
| Magnesium Carbonate | 22.19 |
| Gelatin Solution, 10% weight/weight | 2.38 |
| | 100.00 |

Lozenges having the composition shown in Table 11 were prepared following the procedure of Example 1. These lozenges weighed 2 g. and dissolved in approximately 30 minutes.

Table 11

| Lozenge Formula | |
|---|---|
| Ingredient | Percent |
| Raw Granulation | 91.49 |
| Sodium Carboxymethyl Cellulose | 5.00 |
| Calcium Stearate | 1.00 |
| Talc | 1.00 |
| Flavorant | 1.51 |
| | 100.00 |

EXAMPLE 6

A raw granulation having the composition shown in Table 12 was prepared according to the procedure of Example 4 except that sorbitol was substituted for part of the mannitol.

Table 12

| Raw Granulation | |
|---|---|
| Ingredient | Percent |
| Mannitol Powder | 47.88 |
| Sorbitol Solution, 10% weight/weight | 4.40 |
| Aluminum Hydroxide-Magnesium Carbonate Coprecipitate | 13.57 |
| Magnesium Carbonate | 27.55 |
| Gelatin Solution, 15% weight/weight | 6.60 |
| | 100.00 |

Lozenges having the composition shown in Table 13 were prepared following the procedure of Example 1 except that xanthan gum was substituted for the sodium carboxymethyl cellulose.

Table 13

| Lozenge Formula | |
|---|---|
| Ingredient | Percent |
| Raw Granulation | 93.59 |
| Xanthan Gum | 3.00 |
| Calcium Stearate | 1.00 |
| Talc | 1.00 |
| Flavorant | 1.41 |
| | 100.00 |

The lozenges had a sweet, pleasant taste, as in all of the previous examples, with no unpalatable slimy or gritty mouth feel. They dissolved in approximately 33 minutes in the mouth.

EXAMPLE 7

A raw granulation having the composition shown in Table 14 was prepared according to the procedure of Example 1 except that calcium carbonate was used as the antacid component.

Table 14

| Raw Granulation | |
|---|---|
| Ingredient | Percent |
| Mannitol Powder | 51.80 |
| Calcium Carbonate | 46.04 |
| Gelatin Solution, 10% weight/weight | 2.16 |
| | 100.00 |

Lozenges having a slow dissolving layer and a fast dissolving layer with the composition shown in Tables 15 and 16, respectively, were prepared according to the procedure of Example 2.

Table 15

| Slow Dissolving Layer | |
|---|---|
| Ingredient | Percent |
| Raw Granulation | 90.82 |
| Sodium Carboxymethyl Cellulose | 6.00 |
| Calcium Stearate | 1.00 |
| Talc | 1.00 |
| Sodium Hexametaphosphate | 0.52 |
| Flavorant | 0.66 |
| | 100.00 |

Table 16

| Fast Dissolving Layer | |
|---|---|
| Ingredient | Percent |
| Raw Granulation | 96.60 |
| Calcium Stearate | 1.00 |
| Talc | 1.00 |
| Sodium Hexametaphosphate | 0.52 |
| Flavorant | 0.58 |

Table 16-continued

| Fast Dissolving Layer | |
|---|---|
| Ingredient | Percent |
| Colorant | 0.30 |
| | 100.00 |

The slow dissolving layer is in accordance with the present invention, the fast dissolving layer is not. The lozenges had a pleasant taste with no unpalatable slimy or gritty mouth feel.

EXAMPLE 8

In order to compare the lozenge of this invention prepared in Examples 1 and 7 with a conventional antacid, a cross-over study was made as follows: Ten human subjects participated in each of four groups. Group I subjects received 30 cc. of MAALOX (72 meq.), Group II 60 cc. of MAALOX (144 meq.), Group III one lozenge prepared according to Example 1 (18 meq.) and Group IV one lozenge prepared according to Example 7 (20 meq.).

Before the antacid was administered, a siliconized nasogastric tube was inserted into the gastric puddle. Once the tube was in position, a sample of gastric juice was taken and then returned after the pH had been recorded. This was down 30 minutes, 15 minutes and immediately before the antacid was given to provide three reference points.

The subjects in Groups I and II then ingested the above-indicated amount of MAALOX and the subjects in Groups III and IV sucked on the lozenges of Examples 1 and 7, respectively. The pH of 2 ml. gastric samples was read from time to time and then returned to the stomach. When the pH fell below 3.5, the effect of the antacid was considered over. The results are shown in FIG. 1, Group I being represented by closed triangles, Group II by open circles, Group III by open squares and Group IV by open triangles. Referring to Table 17, it is seen that the new antacid delivery form of the present invention unexpectedly maintains the gastric contents over pH 3.5 twice as long as MAALOX with as little as one-eighth the acid neutralizing capacity.

Table 17

| Dosage Form | Meq. | Time Over pH 3.5 |
|---|---|---|
| 30 cc. MAALOX | 72 | 40.6 |
| 60 cc. MAALOX | 144 | 45.3 |
| Example 1 Lozenge | 18 | 82.8 |

Table 17-continued

| Dosage Form | Meq. | Time Over pH 3.5 |
|---|---|---|
| Example 7 Lozenge | 20 | 77.3 |

From the above it is seen that the present dosage form neutralizes the stomach acid over a considerably longer period of time as compared to conventional antacids with a much smaller amount of antacid.

EXAMPLE 9

In this example it is shown that the magnesium component of an antacid containing a combination of magnesium and aluminum reacts first. When the antacid is in excess, as shown in Table 17, substantially none of the aluminum is reacted. When the antacid is gradually administered in accordance with the present invention, however, both metal components are utilized.

In Test Nos. 1–4, a MAALOX tablet was ground into a powder passing through a 30 mesh screen. The powder was suspended in water and the amount of acid shown in Table 17 added. The solution was filtered and the filtrate, which contained the reacted antacid, was analyzed for magnesium and aluminum content. As shown in Table 17, substantially none of the aluminum was reacted.

Tests Nos. 5–10 were conducted similarly except that in Test 5, 5 ml. of MAALOX liquid was used in place of the powdered MAALOX tablet. In Tests 6–10, a MYLANTA tablet was used in place of the MAALOX tablet.

In Tests Nos. 11–14, a lozenge made in accordance with Example 1 was ground into a powder which passed through a 35 mesh screen. In Tests Nos. 11–12, the powdered lozenge was dissolved in water and the amount of acid shown in Table 17 added, whereas in Tests Nos. 13–14 the antacid was suspended in a small amount of water and added concurrently with the acid. As is shown in Table 17, in Tests Nos. 13–14 both the magnesium and aluminum components of the antacid are utilized. These tests simulate the in vivo benefits obtained with the controlled antacid delivery form of this invention.

In view of the above, it will be seen that the several objects of the invention are achieved and other advantageous results attained. As various changes could be made in the above methods and products without departing from the scope of the invention, it is intended that all matter contained in the above description shall be interpreted as illustrative and not in a limiting sense.

Table 17

| Test No. | Dosage Form | Composition of Dosage Form | | Meq. HCL Added | Meq. Mg++ Ion Reacted | Meq. Al+++ Ion Reacted |
|---|---|---|---|---|---|---|
| | | Meq. Mg Antacid | Meq. Al Antacid | | | |
| 1 | MAALOX Tablet | 6.86 | 5.00 | 2.08 | 1.89 | 0 |
| 2 | MAALOX Tablet | 6.86 | 5.00 | 4.16 | 3.87 | 0 |
| 3 | MAALOX Tablet | 6.86 | 5.00 | 6.24 | 5.65 | 7 parts/million |
| 4 | MAALOX Tablet | 6.86 | 5.00 | 10.40 | 6.65 | 0.78 |
| 5 | MAALOX Liquid | 6.86 | 8.69 | 5.00 | 5.09 | 0 |
| 6 | MYLANTA Tablet | 5.00 | 5.00 | 2.68 | 2.58 | 0 |
| 7 | MYLANTA Tablet | 5.00 | 5.00 | 5.36 | 5.27 | 0 |
| 8 | MYLANTA Tablet | 5.00 | 5.00 | 8.04 | 6.47 | 1.16 |
| 9 | MYLANTA Tablet | 5.00 | 5.00 | 13.40 | 6.87 | 2.39 |
| 10 | MYLANTA II Liquid | 13.72 | 10.00 | 10.00 | 8.55 | 1.28 |
| 11 | Crushed Lozenge Added All At Once | 9.00 | 9.00 | 6.04 | 4.99 | 0 |
| 12 | Crushed Lozenge Added All At Once | 9.00 | 9.00 | 10.10 | 7.23 | 0.94 |
| 13 | Crushed Lozenge | | | | | |

Table 17-continued

| Test No. | Dosage Form | Composition of Dosage Form | | Meq. HCL Added | Meq. Mg++ Ion Reacted | Meq. Al+++ Ion Reacted |
| --- | --- | --- | --- | --- | --- | --- |
| | | Meq. Mg Antacid | Meq. Al Antacid | | | |
| | Slowly Added | 9.00 | 9.00 | 4.72 | 2.22 | 2.31 |
| 14 | Crushed Lozenge | | | | | |
| | Slowly Added | 9.00 | 9.00 | 9.56 | 4.74 | 3.49 |

What is claimed is:

1. A noncariogenic controlled antacid delivery composition compressed into lozenges having a hardness of at least 15 kg/in$^2$, including a mixture of a magnesium antacid salt and an aluminum antacid salt, said salts having different rates of reaction with hydrochloric acid, in a matrix including in combination mannitol, a gel-forming swelling agent selected from the group consisting of sodium carboxymethyl cellulose and xanthum gum, and a hydrophobic magnesium, calcium or aluminum salt of a fatty acid selected from the group consisting of stearic, palmitic, oleic and lauric acids, the mannitol being present in an amount from about 25 to 60 percent by weight, the gel forming agent being present in an amount from about 3 to 10 percent by weight, and the hydrophobic magnesium, calcium or aluminum salt of a fatty acid being present in an amount from about 1 to 5 percent by weight, to provide a lozenge which dissolves in about 15 to 60 minutes in a user's mouth, each of said lozenges containing an effective amount of antacid salts to maintain the pH of the user's gastric juice above 3.5.

2. A delivery system according to claim 1 wherein the lozenge weighs from about 1 to 3 grams.

3. A delivery system according to claim 2 wherein the lozenge is comprised of at least two layers, each having a different dissolution rate.

4. A delivery system according to claim 3 wherein the lozenge has a neutralizing capacity of about 15 to 40 meq.

* * * * *